United States Patent [19]

Coffen

[11] 4,193,928
[45] Mar. 18, 1980

[54] LASALOCID DERIVATIVES

[75] Inventor: David Coffen, Glen Ridge, N.J.

[73] Assignee: Hoffmann-La Roche Inc., Nutley, N.J.

[21] Appl. No.: 921,645

[22] Filed: Jul. 3, 1978

Related U.S. Application Data

[63] Continuation-in-part of Ser. No. 836,350, Sep. 26, 1977, abandoned.

[51] Int. Cl.² .................. C07D 309/06; C07D 309/04; C07D 213/70
[52] U.S. Cl. ...................... 260/345.7 R; 260/345.9 R; 260/345.8 R; 260/326.8; 544/149; 546/268; 546/207; 546/152; 424/283; 424/263; 548/187
[58] Field of Search ................. 260/345.7 R, 345.8 R, 260/345.9 R; 546/268

[56] References Cited

U.S. PATENT DOCUMENTS

3,715,372  2/1973  Stempel et al. ............... 260/345.8 R

*Primary Examiner*—Nicky Chan

*Attorney, Agent, or Firm*—Jon S. Saxe; Bernard S. Leon; Frank P. Hoffman

[57] ABSTRACT

There is presented compounds of the formula

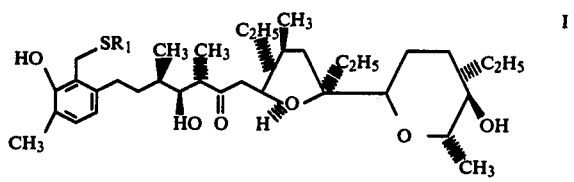

wherein $R_1$ is selected from the group consisting of aryl, substituted aryl, aralkyl, heteroaryl, cycloalkyl, lower alkyl, lower alkenyl, carboxy lower alkyl, carboalkoxy lower alkyl, aminoalkyl, substituted aminoalkyl, hydroxyalkyl, alkoxy alkyl, thioalkoxy alkyl and hydrogen.

These compounds exhibit pharmacological activity as antihypertensive agents.

Also presented are novel intermediates leading to the end products and a process to produce the end products.

13 Claims, No Drawings

LASALOCID DERIVATIVES

This application is a continuation-in-part of Ser. No. 836,350, filed 9/26/77 now abandoned.

DESCRIPTION OF THE INVENTION

The present invention relates to compounds of the formula

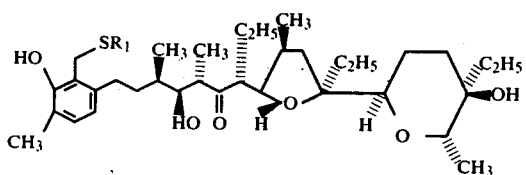

wherein $R_1$ is selected from the group consisting of aryl, substituted aryl, heteroaryl, aralkyl, cycloalkyl, lower alkyl, carboalkoxy lower alkyl, aminoalkyl, substituted aminoalkyl, hydroxy alkyl, alkoxy alkyl, thioalkoxy alkyl, carboxy lower alkyl and hydrogen.

By the term "lower alkyl" or "alkyl" as utilized herein, either alone or in combination with another radical, straight or branched chain hydrocarbon groups containing 1 to 16 carbon atoms, preferably $C_1$ to $C_7$, in the chain are contemplated. Representative of lower alkyl groups are methyl, ethyl, isopropyl, tertiary butyl and the like.

By the term "aryl" is meant an unsubstituted monocarbocyclic aromatic moiety, such as, phenyl, and the like.

By the term "substituted aryl" is meant a tolyl, halo, alkoxy or nitro mono or disubstituted phenyl and the like.

By the term "alkoxy" is meant straight or branched chain saturated hydrocarbonoxy group containing from 1 to 7 carbon atoms, preferably from 1 to 4 carbon atoms, such as methoxy, ethoxy, propoxy and the like.

The term "halogen" or "halo" is used to include all four forms thereof, i.e., chlorine, bromine, fluorine and iodine.

By the term "cycloalkyl" is meant a cyclized moiety of 4 to 7 carbon atoms, e.g., cyclohexyl, etc.

By the term "heteroaryl" is meant an unsubstituted mono-heterocyclic aromatic moiety, such as, pyridyl, furyl and the like.

By the term "aralkyl" is meant a straight or branched chain alkyl substituted by a mono-carbocyclic moiety, such as, benzyl.

By the term "lower alkenyl" is meant a straight or branched chain hydrocarbon group which contains an olefinic double bond having from 2 to 6 carbon atoms.

By the term "carboxy lower alkyl" is meant a compound of the formula

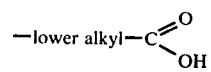

wherein the lower alkyl is branched or straight chain and connected to the thio group.

By the term "carbalkoxy lower alkyl" is meant a compound of the formula

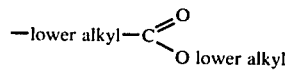

wherein the lower alkyl group is branched or straight chain and connected to the thio group.

By the term "aminoalkyl and substituted aminoalkyl" is meant a radical of the formula

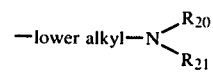

wherein $R_{20}=R_{21}=$ hydrogen or lower alkyl.

By the term "hydroxy alkyl" is meant a radical of the formula

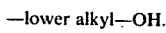

By the term "alkoxy alkyl" is meant a radical of the formula

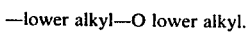

By the term "thioalkoxy alkyl" is meant a radical of the formula

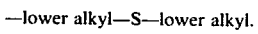

When various moieties set forth below are to form a part of a heterocyclic ring, it is intended that the moieties, together with the nitrogen atom to which they are attached form, preferably, a 5 or 6 membered ring which contains at the most one additional hetero atom, preferably nitrogen, sulfur or oxygen as the hetero atom. Thus, by the heterocyclic ring, there is intended such moieties as morpholino, piperazino, piperidino and pyrrolidino.

Lasalocid is a known antibiotic having been disclosed together with a method for its preparation in U.S. Pat. Nos. Re. 29,244 issued May 31, 1977 to Berger et al., 3,715,372 issued Feb. 6, 1973 and 3,944,573 issued Mar. 16, 1976.

Lasalocid may be converted into the derivatives of formula I by the following general reaction scheme:

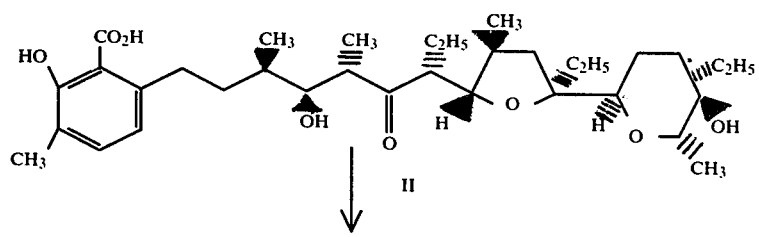

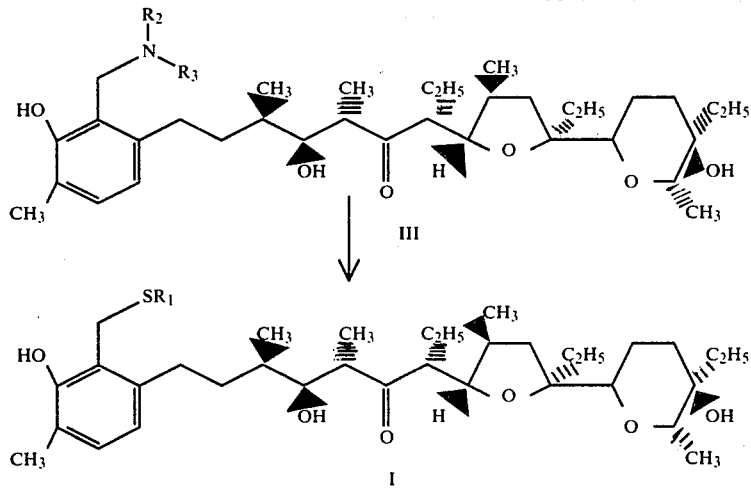

wherein $R_1$ is as above and $R_2$ and $R_3$ is lower alkyl, cyclolower alkyl or a 5 or 6 membered heterocyclic ring.

II→III

The conversion of the starting material of formula II (Lasalocid) to a compound of formula III is accomplished by a Mannich reaction, specifically by the reaction of a mixture of a dialkylamine or a cyclic amine such as, morpholine, piperidine, pyrrolidine, etc. and para formaldehyde or aqueous formaldehyde. Solvents suitable for such a reaction include $C_1$ to $C_4$ alcohols, toluene, benzene, chlorinated hydrocarbons and ethers, such as, dioxane or tetrahydrofuran. The reaction temperature may be varied from 60° C. to the reflux temperature of the solvent utilized with reflux temperature preferred.

III→I

The compound of formula III is thereafter converted into the desired thio derivative by the reaction of the compound of formula III with a suitable weak base, i.e., one sufficient to generate the orthoquinone methide and the conjugate base of the selected mercaptan i.e., $R_1S^\ominus$ while not causing the retroaldol cleavage of the lasalocid molecule. Suitable bases include alkali metal e.g., sodium or potassium carbonates and bicarbonates trialkylamines or pyridine. Solvents suitable for such a reaction include alcohols, e.g., methanol or ethanol, high boiling ethers, dioxane or tetrahydrofuran and ethyl acetate. The reaction temperature may vary between room temperature and reflux temperature with reflux temperature of the selected solvent as preferred. Reactants to provide the $-SR_1$ substituents which are preferred include thiophenol, p-chlorothiophenol, cyclohexyl mercaptan, benzyl mercaptan and mercaptoacetic acid to provide for example the thiophenyl, p-chlorothiophenyl, thiocyclohexyl, thiobenzyl and mercaptoacetic moieties, respectively. The above mercaptans are preferred but not limiting embodiments of the invention.

Using a control as a standard for comparison, 1-(phenylthiomethyl)-1-decarboxylasalocid was tested and exhibited for anti-hypertensive activity. The tests were conducted utilizing single oral dosages in the DOCA-Na rat over a five-day period with dosing discontinued thereafter. Blood pressure monitoring was carried out for the five-day period and daily after cessation of dosing until blood pressure returned to pre-drug levels. The daily dosage was 10 mg/kg/day. From these results, it is apparent that differences exist in onset and duration of anti-hypertensive activity and potency but that the 1-(phenylthiomethyl)-1-decarboxylasalocid exhibited antihypertensive activity when compared to the control. The results are as follows:

| | Dose (mg/kg p.o.) | N | Oral Antihypertensive Activity of 1-(phenylthiomethyl)-1-descarboxylasalocid (5-day administration) in DOCA-Na Rats[a] | | | | | | | | | |
|---|---|---|---|---|---|---|---|---|---|---|---|---|
| | | | Systolic Blood Pressure (mm Hg) | | | | | | | | | |
| | | | Day 1 | | Day 2 | | Day 3 | | Day 4 | | Day 5 | |
| | | | AM | PM | AM | PM | AM | PM | AM | PM | AM | PM |
| Vehicle | — | 5 | 203 ± 2 | 194 ± 4 | 198 ± 5 | 188 ± 9 | 201 ± 4 | 195 ± 4 | 205 ± 4 | 193 ± 7 | 200 ± 4 | 188 ± 5 |
| 1-phenylthio-methyl)-1-descarboxy-lasalocid | 10.0 | 12 | 212 ± 5 | 181 ± 8 | 172 ± 6 | 160 ± 6 | 173 ± 4 | 160 ± 3 | 173 ± 5 | 151 ± 9 | 159 ± 7 | 151 ± 4 |
| | | | Heart Rate (beats/min.) | | | | | | | | | |
| Vehicle | — | 5 | 410 ± 19 | 404 ± 9 | 406 ± 23 | 400 ± 13 | 404 ± 29 | 424 ± 24 | 442 ± 28 | 434 ± 22 | 434 ± 17 | 400 ± 20 |
| 1-(phenylthio-methyl)-1-descarboxy-lasalocid | 10.0 | 12 | 428 ± 17 | 433 ± 17 | 435 ± 14 | 424 ± 19 | 414 ± 11 | 386 ± 11 | 410 ± 11 | 384 ± 12 | 403 ± 11 | 374 ± 12 |

[a]DOCA-Na hypertensive male rats received single oral doses of either vehicle (5% acacia) or 1-(phenylthiomethyl)-1-descarboxylasalocid in acacia for 5 consecutive days. Systolic blood pressure and heart rate readings were obtained prior to (AM) and 6 hours after (PM) vehicle or drug. N stands for number of test animals utilized.

1-[(carboxymethyl thiomethyl]-1-decarboxylasalocid,
1-(p-chlorophenylthiomethyl)-1-decarboxylasalocid, 1-(benzylthiomethyl)-1-decarboxylasalocid and 1-(cyclohexylthiomethyl)-1-decarboxylasalocid were also tested for antihypertensive activity.

The tests were conducted utilizing single oral dosages in the DOCA-Na rat over a five-day period with dosing discontinued thereafter. Blood pressure monitoring was carried out for the five-day period and daily after cessation of dosing until blood pressure returned to pre-drug levels. The daily dosage was 10 mg/kg/day. From these results, it is apparent that differences exist in onset and duration of antihypertensive activity and potency but that the above compounds exhibited antihypertensive activity when comparing the blood pressure of Day 1 with that of Day 5 upon cessation of treatment. The results are as follows:

ples, it should be recognized that all of the compounds disclosed in the specification as being useful may be substituted therefor.

| CAPSULE FORMULATION | | | | |
|---|---|---|---|---|
| | mg/cap | mg/cap | mg/cap | mg/cap |
| 1. 1-(phenylthiomethyl)-1-decarboxylasalocid | 0.1 | 1.0 | 5.0 | 10.0 |
| 2. Polyvinylpyrrolidone | 20.0 | 20.0 | 20.0 | 20.0 |
| 3. Modified Starch | 55.0 | 55.0 | 55.0 | 55.0 |
| 4. Lactose | 167.4 | 166.5 | 212.5 | 257.5 |
| 5. Dioctyl Sodium Sulfosuccinate | 1.5 | 1.5 | 1.5 | 1.5 |
| 6. Talc | 5.0 | 5.0 | 5.0 | 5.0 |
| 7. Magnesium Stearate | 1.0 | 1.0 | 1.0 | 1.0 |
| Capsule Fill Weight | 250 mg. | 250 mg. | 300 mg. | 350 mg. |

Effect of Listed Compounds on Systolic Blood Pressure and Heart Rate in the Conscious DOCA-Na Hypertensive Rat[a]

| Compound | Dose (mg/kg p.o.) | N | Systolic Blood Pressure (mm Hg) | | | | | | | | | |
|---|---|---|---|---|---|---|---|---|---|---|---|---|
| | | | Day 1 | | Day 2 | | Day 3 | | Day 4 | | Day 5 | |
| | | | AM | PM | AM | PM | AM | PM | AM | PM | AM | PM |
| 1-[(carboxymethyl thiomethyl]-1-decarboxylasalocid | 10 | 6 | 226 ± 3 | 204 ± 6 | 208 ± 4 | 206 ± 6 | 207 ± 12 | 196 ± 10 | 209 ± 6 | 192 ± 7 | 211 ± 8 | 202 ± 9 |
| 1-(p-chlorophenylthiomethyl-1-decarboxylasalocid | 10 | 6 | 221 ± 3 | 194 ± 9 | 180 ± 11 | 171 ± 12 | 189 ± 8 | 171 ± 9 | 203 ± 11 | 187 ± 8 | 209 ± 6 | 207 ± 3 |
| 1-(benzylthiomethyl)-1-decarboxylasalocid | 10 | 6 | 203 ± 4 | 186 ± 3 | 201 ± 2 | 181 ± 5 | 192 ± 4 | 187 ± 2 | 198 ± 4 | 203 ± 3 | 194 ± 2 | 199 ± 4 |
| 1-(cyclohexylthiomethyl)-1-decarboxylasalocid | 10 | 6 | 207 ± 4 | 180 ± 7 | 201 ± 5 | 184 ± 6 | 200 ± 11 | 172 ± 7 | 196 ± 9 | 182 ± 9 | 204 ± 4 | 187 ± 6 |

[a]DOCA-Na hypertensive male rats received single oral doses of each compound for 5 consecutive days. Systolic blood pressure and heart rate readings were obtained prior to (AM) and 6 hours after (PM) drug. N stands for the number of test animals utilized.

| Compound | Dose mg/kg p.o. | N | Heart Rate (beats/min.) | | | | | | | | | |
|---|---|---|---|---|---|---|---|---|---|---|---|---|
| | | | Day 1 | | Day 2 | | Day 3 | | Day 4 | | Day 5 | |
| | | | AM | PM | AM | PM | AM | PM | AM | PM | AM | PM |
| 1-[(thiomethyl)-carboxymethyl]-1-decarboxylasalocid | 10 | 6 | 430 ± 13 | 430 ± 14 | 435 ± 14 | 448 ± 20 | 405 ± 18 | 403 ± 16 | 422 ± 24 | 417 ± 17 | 430 ± 27 | 402 ± 20 |
| 1-(p-chlorophenylthiomethyl)-1-decarboxylasalocid | 10 | 6 | 435 ± 13 | 422 ± 18 | 388 ± 17 | 382 ± 16 | 400 ± 21 | 375 ± 16 | 387 ± 19 | 397 ± 20 | 418 ± 14 | 357 ± 11 |
| 1-benzylthiomethyl)-1-decarboxylasalocid | 10 | 6 | 455 ± 15 | 445 ± 11 | 438 ± 17 | 465 ± 15 | 425 ± 7 | 442 ± 17 | 423 ± 3 | 420 ± 14 | 435 ± 12 | 410 ± 13 |
| 1-(cyclohexylthiomethyl-1-decarboxylasalocid | 10 | 6 | 452 ± 16 | 441 ± 22 | 455 ± 16 | 407 ± 17 | 430 ± 24 | 418 ± 16 | 403 ± 15 | 415 ± 19 | 448 ± 15 | 408 ± 8 |

[a]DOCA-Na hypertensive male rats received single oral doses of each compound for 5 consecutive days. Systolic blood pressure and heart rate readings were obtained prior to (AM) and 6 hours after (PM) drug. N stands for the number of test animals utilized.

The following represents tablet and capsule formations which may be utilized to administer the required dosage of active ingredient. Although 1-(phenylthiomethyl)-1-decarboxylasalocid, a preferred compound of the present invention, is utilized in the following exam-

Procedure:

1. Mix items 1, 3 and 5 is a suitable mixer.
2. Dissolve items 2 and 5 in distilled water and/or alcohol and granulate to proper consistency. Mill.
3. Dry in a suitable oven.
4. Mill and mix with talc and magnesium stearate for 3 minutes.
5. Encapsulate on suitable machine.

| TABLET FORMULATION: - (Wet Granulation) | | | | |
|---|---|---|---|---|
| | mg/tablet | mg/tablet | mg/tablet | mg/tablet |
| 1. 1-(phenylthiomethyl)-1-decarboxylasalocid | 0.1 | 1 | 5 | 10 |
| 2. Lactose | 202.9 | 202 | 232 | 261 |
| 3. Modified Starch | 25 | 25 | 35 | 45 |
| 4. Pregelatinized Starch | 20 | 20 | 25 | 30 |
| 5. Distilled Water q.s. | — | — | — | — |
| 6. Magnesium Stearate | 2 | 2 | 3 | 4 |
| Weight of Tablet | 250 mg. | 250 mg. | 300 mg. | 350 mg. |

Procedure:

1. Mix items 1–4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with approximate punches.

For use as antihypertensive agents, and in reverting the hemodynamic profile to normal, the active agents are formulated, using conventional inert pharmaceutical adjuvant materials, into dosage forms which are suitable for oral administration. Other dosage forms, e.g., parenteral, may be possible. The oral dosage forms include tablets, capsules, dragees, suspensions, solutions and the like. The identity of the inert adjuvant materials which are used in formulating the active ingredients into oral dosage forms will be immediately apparent to persons skilled in the art. These adjuvant materials, either inorganic or organic in nature, include, for example, gelatin, albumin, lactose, starch, magnesium stearate, preservatives (stabilizers), melting agents, emulsifying agents, salts for altering osmotic pressure, buffers, etc., which can be incorporated, if desired, into such formulations.

It has been found that subacute oral administration for treatment of hypertension of the active ingredient, i.e., dosing up to five (5) days with discontinuance thereafter, in a warm-blooded animal, e.g., the DOCA Na hypertensive rat, is most effective when the dose level is within the range of about 5 mg/kg/day to about 100 mg/kg/day, more preferably about 5 mg/kg/day to about 10 mg/kg/day. Chronic oral administration of the active ingredient, i.e., dosing over five (5) days, is most effective when a low dose level is utilized, i.e., less than 0.1 mg/kg/day, e.g., 0.01 mg/kg/day to about 5 mg/kg/day. The above dosage regimens may also be utilized when treating other cardiovascular problems such as angina, claudication and decreased blood flow to the brain. Treatment of these problems is thought to be positively affected due to the fact that arterial blood flow would be enhanced by increasing pulse wave velocity secondary to increasing compliance so that blood flow is regulated by a pressure gradient rather than kinetic energy.

Of the above dosage regimens, most preferred is the chronic low level administration of the active ingredient, i.e., less than 0.1 mg/kg/day to about 5 mg/kg/day. The dosage administered to a particular individual should be varied within the above dosage range, based on the toxicity of the particular polyether. The desired antihypertensive effect must be a function of the particular compound's potency, and the weight and physical condition of the individual patient. Therefore, an effective dosage amount of active compound may be determined by the clinician utilizing his best judgment on the patient's behalf.

EXAMPLE 1

1-(Diethylaminomethyl)-1-descarboxylasalocid

A mixture of lasalocid ethanolate (5.0 g), paraformaldehyde (2.5 g), and diethylamine (2.5 g) in toluene (200 ml) was stirred and heated at reflux for 90 min. Water was collected in a trap during the reflux period. The resulting solution was diluted with ether and transferred to a separatory funnel. It was washed with water and then with very dilute (ca. 0.05 N) hydrochloric acid. The organic layer was dried, filtered, and the solvent was removed under reduced pressure leaving a pale yellow (sometimes colorless) resin. This crude Mannich base contains residual toluene but was used directly in the next step.

EXAMPLE 2

1-(Phenylthiomethyl)-1-descarboxylasalocid

A solution of the Mannich base of Example 1 (9.7 g), thiophenol (4.5 ml), and triethylamine (4 ml) in ethanol (125 ml) was heated at reflux for 18 hours. The solvent was evaporated under reduced pressure and the residue was taken up in $CH_2Cl_2$. After washing with water and dilute aq. $Na_2CO_3$, the solution was dried and the solvent evaporated. The crude product was purified by chromatography on a silica gel (200 g) column. Hexane/ethyl acetate 8:1 eluted the thiophenol and hexane/ethyl acetate 6:1 was used to elute the product. Evaporation of solvent, finally with a vacuum pump, afforded colorless foam.

EXAMPLE 3

1-(p-Chlorophenylthiomethyl)-1-decarboxylasalocid

A solution of 1-(diethylaminomethyl)-1-decarboxylasalocid (1.4 g), p-chlorothiophenol (2 g), and triethylamine (2 ml) in ethanol (50 ml) was heated at reflux for 18 hours. Since the reaction was incomplete (tlc), additional p-chlorothiophenol (2 g) and triethylamine (2 ml) were added and reflux continued for 24 hours more. After cooling, the solvent and amine were evaporated under reduced pressure and the residue was taken up in methylene chloride. This solution was washed with aq. $Na_2CO_3$ solution, dried over $Na_2SO_4$ and evaporated.

The residue which was a mixture, mainly of p-chlorothiophenol and the desired thioether, was chromatographed on silica gel using benzene/ethyl acetate (2:1) as the eluting solvent. The fractions containing the desired product (tlc) were combined and evaporated giving a colorless, solid foam which "melted" at 42°–46°.

EXAMPLE 4

1-(Cyclohexylthiomethyl)-1-decarboxylasalocid 1-(Diethylaminomethyl)-1-decarboxylasalocid (1,4 g), cyclohexyl mercaptan (2 ml), and triethylamine (2 ml) were combined in ethanol (50 ml) and the solution was heated to reflux. Using the same procedure described in Example 3 including the addition of more cyclohexyl mercaptan and triethylamine after 18 hours, the product was obtained as a colorless, solid foam after purification by column chromatography on silica gel.

EXAMPLE 5

1-(Benzylthiomethyl)-1-decarboxylasalocid 1-(Diethylaminomethyl)-1-decarboxylasalocid (4.5 g), benzyl mercaptan (5 ml), and triethylamine (5 ml) were combined in ethanol (100 ml) and the solution was heated to reflux overnight. After cooling and evaporation of solvent under reduced pressure, the residue was chromatographed on silica gel using hexane/ethyl acetate (5:1) as the eluting solvent. The fractions containing the desired product were combined and evaporated giving the end product. The product was contaminated with small amounts of benzyl mercaptan and was further purified by preparative layer chromatography on six 20×20 cm silica gel plates, using hexane/ethyl acetate 4:1 as the developing solvent. Pure product was obtained as colorless, solid foam.

EXAMPLE 6

1-(Carboxymethyl Thiomethyl)-1-decarboxylasalocid

A solution of the Mannich base of Example 1 (3g), mercaptoacetic acid (3ml), and triethylamine (3ml) in ethanol 100 ml was heated at reflex for 36 hours. The ethanol was then removed by evaporation under reduced pressure and the residue in, $CH_2Cl_2$ solution, was washed with dilute aqueous $Na_2CO_3$, water, 0.5N HCl, and finally with water again. After drying and evaporation, the crude product was purified by chromatography on silica gel using 4% MeOH in $CHCl_3$ as the eluting solvent. Since the product was found to absorb ions from inorganic material, the eluate containing the product was washed with very dilute HCl before evaporation. This gave colorless foam as end product.

EXAMPLE 7

1-Mercaptomethyl-1-decarboxylasalocid

A solution of 1-(diethylaminomethyl)-1-decarboxylasalocid (1.85 g) and triethylamine (2 ml) in ethanol (50 ml) was heated at reflux for 32 hr while bubbling a slow stream of hydrogen sulfide through the solution. Evaporation of solvent under reduced pressure left a residue which was chromatographed on preparative layer plates (20×20 cm, silica gel). The desired product was obtained as a colorless, solid foam.

EXAMPLE 8

1-(Methylthiomethyl)-1-decarboxylasalocid

A solution of 1-(diethylaminomethyl)-1-decarboxylasalocid (1 g) and triethylamine (2 ml) in ethanol (50 ml) was heated at reflux for 8 hr while passing in gaseous methyl mercaptan. Evaporation and purification by preparative layer chromatography afforded 300 mg of the desired compound as a colorless, solid foam.

EXAMPLE 9

1-(2-Furylmethylthiomethyl)-1-decarboxylasalocid

A solution of 1-(diethylaminomethyl)-1-decarboxylasalocid (1.4 g), furfuryl mercaptan (2 ml) and triethylamine (2 ml) in ethanol (50 ml) was heated at reflux for 42 hrs with addition of more base and mercaptan (2 ml of each) after 18 hours. Evaporation and purification by preparative layer chromatography afforded the desired product as a colorless, solid foam.

EXAMPLE 10

Following the procedure described above and by using the appropriate commercially available thiol, compounds may also be prepared in which $R_1$ is allyl, 2-aminophenyl, 4-aminophenyl, 4-bromo-3-methylphenyl, 4-bromophenyl, 1-butyl, 2-butyl, tert-butyl, isobutyl, carboethoxymethyl, carbomethoxymethyl, 2-carboxyethyl, o-carboxyphenyl, 4-chlorobenzyl, 2-n-decylaminoethyl, 2,5-dichlorophenyl, 3,4-dichlorophenyl, 2-diethylaminoethyl, 2-diisopropylaminoethyl, 1-dodecyl, ethyl, 4-fluorophenyl, n-heptyl, n-hexadecyl, 2-hydroxyethyl, 2-ethoxyethyl, 2-ethylthioethyl, 1-methyl-2-imidazyl, 2,3-dihydroxypropyl, 2-pyridyl, 4-pyridyl, 3-hydroxy-2-pyridyl, 2-thiazolyl, 2-methoxyphenyl, 3-methoxyphenyl, 4-methoxyphenyl, 2-methyl-2-butyl, 3-methyl-1-butyl, 4-nitrophenyl, 1-nonyl, 1-octyl, pentachlorophenyl, pentafluorophenyl, 1-pentyl, 3-phenyl-1-propyl, 1-propyl, 2-propyl, 2-quinolyl, 2,3,5,6-tetrafluorophenyl, p-tolyl, 2,4,5-trichlorophenyl, 7-trifluoromethyl-4-quinolyl, or triphenylmethyl.

What is claimed:

1. A compound of the formula

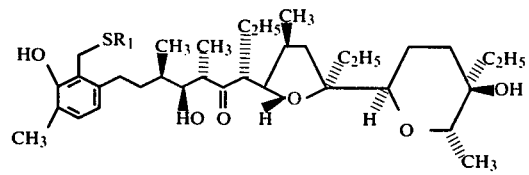

wherein $R_1$ is selected from the group consisting of phenyl, tolyl or halo, alkoxy or nitro mono-or disubstituted phenyl, benzyl, pyridyl, furyl, $C_4$ to $C_7$ cycloalkyl, lower alkyl, $C_2$ to $C_6$ lower alkenyl,

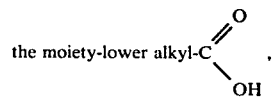

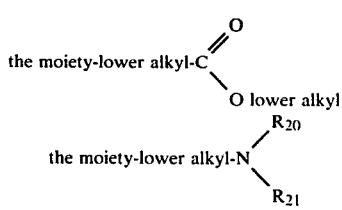

wherein $R_{20}$ and $R_{21}$ are hydrogen or lower alkyl, hydroxy lower alkyl, alkoxyalkyl, the moiety-lower alkyl-S-lower alkyl and hydrogen.

2. The compound of claim 1 wherein $R_1$ is phenyl.

3. The compound of claim 1 wherein $R_1$ is tolyl or halo, alkoxy or nitro mono- or di-substituted phenyl.

4. The compound of claim 1 wherein $R_1$ is benzyl.

5. The compound of claim 1 wherein $R_1$ is $C_4$ to $C_7$ cycloalkyl.

6. The compound of claim 1 wherein $R_1$ is lower alkyl.

7. The compound of claim 1 wherein $R_1$ is

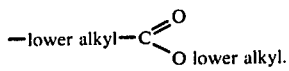

8. A compound of the formula: 1-(p-Chlorophenylthiomethyl)-1-decarboxylasalocid.

9. A compound of the formula: 1-(Cyclohexylthiomethyl)-1-decarboxylasalocid.

10. A compound of the formula: 1-(Benzylthiomethyl)-1-decarboxylasalocid.

11. A compound of the formula: 1-(Carboxymethylthiomethyl)-1-decarboxylasalocid.

12. A compound of the formula: 1-(Phenylthiomethyl)-1-decarboxylasalocid.

13. The compound of claim 1 wherein $R_1$ is hydrogen.